United States Patent [19]
Doyle, Jr.

[11] 3,970,652
[45] July 20, 1976

[54] SELECTIVELY HERBICIDAL 2-SUBSTITUTED-4H-3,1-BENZOXAZIN-4-ONES

[75] Inventor: William C. Doyle, Jr., Leawood, Kans.

[73] Assignee: Gulf Research & Development Company, Pittsburgh, Pa.

[22] Filed: June 2, 1972

[21] Appl. No.: 259,241

Related U.S. Application Data

[62] Division of Ser. No. 886,403, Dec. 18, 1969, Pat. No. 3,914,121.

[52] U.S. Cl.............................. 260/244 R; 71/88; 71/90
[51] Int. Cl.² ...................................... C07D 265/22
[58] Field of Search .................................... 260/244

[56] References Cited
UNITED STATES PATENTS
3,357,977  12/1967  Errede .............................. 260/244

OTHER PUBLICATIONS

Bogentoff et al., Acta Pharm. Suecica, vol. 6, pp. 489–500 (1969).
Legrand, Bull. Soc. Chim. France, pp. 337–343 (1960).

Primary Examiner—Harry I. Moatz
Attorney, Agent, or Firm—Carl A. Cline

[57] ABSTRACT

Unwanted vegetation is combated in the presence of grain crops and soybeans by post-emergent application of one or more of the following compounds:
2-(m-chlorophenyl)-4H-3,1-benzoxazin-4-one,
2-(m-trifluoromethylphenyl)-4H-3,1-benzoxazin-4-one,
2-(2-thienyl)-4H-3,1-benzoxazin-4-one,
2-(o-trifluoromethylphenyl)-4H-3,1-benzoxazin-4-one,
2-(p-trifluoromethylphenyl)-4H-3,1-benzoxazin-4-one,
2-(4-methyl-1,2,3-thiadizole-5-yl)-benzoxazin-4-one
2-(m-bromophenyl)-4H-3,1-benzoxazin-4-one.

4 Claims, No Drawings

SELECTIVELY HERBICIDAL 2-SUBSTITUTED-4H-3,1-BENZOXAZIN-4-ONES

DESCRIPTION OF THE INVENTION

This is a division of application Ser. No. 886,403, filed Dec. 18, 1969, now U.S. Pat. No. 3,914,121.

2-Aryl-4H-3,1-benzoxazin-4-ones have been suggested as selective herbicides, for example, in French Pat. No. 1.373.264. Many compounds of this type have virtually no herbicidal activity, however. By way of illustration, the following compounds appear to be practically non-toxic to ordinary plants:

2-(3,4-dichlorophenyl)-4H-3,1-benzoxazin-4-one; m.p. 176°–7°
2-(m-nitrophenyl)-4H-3,1-benzoxazin-4-one; m.p. 168°–70°
2-(p-nitrophenyl)-4H-3,1-benzoxazin-4-one; m.p. 197°–8°
2-(m-fluorosulfonylphenyl)-4H-3,1-benzoxazin-4-one; m.p. 117°–118°
2-(1-naphthyl)-4H-3,1-benzoxazin-4-one; m.p. 138°–40°
2-(3,5-dimethylphenyl)-4H-3,1-benzoxazin-4-one; m.p. 196°–8°
2-(4,5-dibromo-2-thienyl)-4H-3,1-benzoxazin-4-one; m.p. 222°–3°
2-(2-biphenylyl)-4H-3,1-benzoxazin-4-one; m.p. 118°–20°
2-(m-chlorophenyl)-6-methyl-4H-3,1-benzoxazin-4-one; m.p. 163°–4°

Other compounds of this type must be applied in such large quantities to obtain toxic effect that they cannot be seriously considered for herbicidal use. Examples of such compounds are:

7-nitro-2-phenyl-4H-3,1-benzoxazin-4-one; m.p. 181°–3°
2-(o-methoxyphenyl)-4H-3,1-benzoxazin-4-one; m.p. 132°–3°
2-(p-methoxyphenyl)-4H-3,1-benzoxazin-4-one; m.p. 154°–5°

(all melting points disclosed herein are in degrees C.)

In general, when considered from the standpoint of selective phytotoxic effect, the 2-aryl-4H-3,1-benzoxazin-4-ones are extremely varied in behavior and are lacking in promise of commercial utility.

I have discovered a small group of compounds, however, which are useful in combating unwanted vegetation in grains, most of these compounds also being useful for combating broadleaf weeds in soybeans, a much-desired and comparatively rare characteristic.

These compounds are:
2-(m-chlorophenyl)-4H-3,1-benzoxazin-4-one; m.p. 159°–60°
2-(m-trifluoromethylphenyl)-4H-3,1-benzoxazin-4-one; m.p. 129°–130.5°
2-(2-thienyl)-4H-3,1-benzoxazin-4-one; m.p. 139°–41°
2-(o-trifluoromethylphenyl)-4H-3,1-benzoxazin-4-one; m.p. 100°–101°
2-(p-trifluoromethylphenyl)-4H-3,1-benzoxazin-4-one; m.p. 104°–5°, and
2-(4-methyl-1,2,3-thiadiazol-5-yl)-4H-3,1-benzoxazin-4-one; m.p. 168°–9°

One known compound, 2-(m-bromophenyl)-4H-3,1-benzoxazin-4-one; m.p. 161°–2°, is also useful in combating broadleaf weeds in soybeans.

The compounds in this series were prepared in good yield by the method of Bain and Smalley, J. Chem. Soc. (c) 1968, 1593, as illustrated by the following description of the preparation of 2-(m-chlorophenyl)-4H-3,1-benzoxazin-4-one.

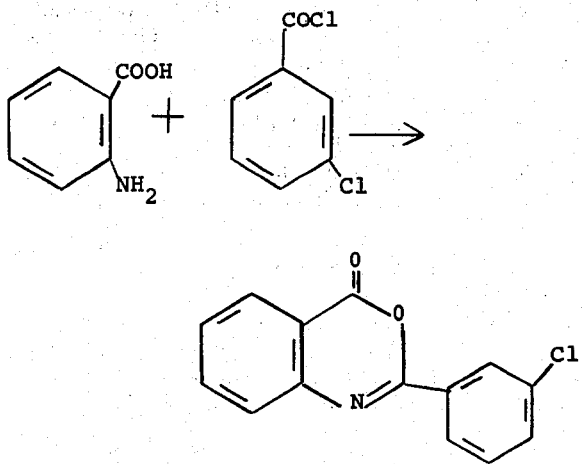

To a stirred solution of 76.5 g (0.56 mole) of anthranilic acid in 1000 ml of pyridine at room temperature was added 197 g (1.12 mole) of m-chlorobenzoyl chloride at a rapid dropwise rate. The temperature rose to 45°–50° and, midway through the addition, a precipitate began forming. After stirring one hour at room temperature the slurry was poured into 1500 ml of water and the precipitate was filtered, washed well with water and air dried to give 139 g (96.5%) of 2-(m-chlorophenyl)-4H-3,1-benzoxazin-4-one, m.p. 158°–60°. Crystallization from ethanol gave an analytical sample, m.p. 159°–60°.

USE OF THE HERBICIDES

So as to illustrate clearly the selective phytotoxic properties of the herbicides, a group of controlled greenhouse experiments is described below.

1. Post Emergent Use

An aqueous dispersion of each active compound was prepared by combining 0.4 gram of the compound with about 4 ml. of a solvent-emulsifier mixture (3 parts of a commercial polyoxyethylated vegetable oil emulsifier, one part xylene, one part kerosene) and then adding water, with stirring, to a final volume of 40 ml.

The species of plants on which each compound was to be tested were planted in four-inch pots in a greenhouse. Ten to 18 days after emergence of the plants, three pots of each species were sprayed with an aqueous dispersion of the active compound prepared as described above, at a rate of 5 lb. of active compound per acre and at a spray volume of 60 gallons per acre. Approximately one week after the spray application the plants were observed and the results rated according to the following schedule:

DEGREE

0 = no effect
1 = slight effect
2 = moderate effect
3 = severe effect
4 = maximum effect (all plants died)

The same rating schedule was employed to judge pre-emergent results obtained according to the procedure below.

2. Pre-Emergent Use

A solution of each active compound was prepared by dissolving 290 mg of the compound to be tested in 200 ml of acetone. Disposable paper trays about 2½ inches deep of molded pulp were prepared and seeded with a variety of species of plant seeds, then sprayed with the acetone solution at the rate of 10 lb of active chemical per acre of sprayed area. One tray, which had been seeded with alfalfa, brome, flax, oats, radishes and sugar beets was held at 75°F day temperature; another seeded with corn, coxcomb, cotton, crabgrass, millet and soybeans was held at 85°F. Twenty-one days after seeding and treatment the plantings were examined and herbicidal effect was rated according to the above schedule.

Both post-emergent and pre-emergent results are set forth in the following table.

ticularly useful in combination with other herbicides which are employed in combating weeds in these crops.

The p-trifluoromethylphenyl compound, by contrast, kills a large number of species of weeds which occur in oats, corn, wheat and grain sorghum fields but appears to have no utility for combating weeds in soybeans.

The 2-thienyl compound is particularly interesting because of its ability to kill both grasses and broadleaf weeds in soybean fields.

The m-chlorophenyl compound has the ability to combat broadleaf weeds such as pigweed in the presence of an unusual number of crops, including such sensitive plants as soybeans, sugar beets and tomatoes. The o-chlorophenyl and p-chlorophenyl compounds do not possess this interesting selectivity. The p-chlorophenyl compound is deficient in phytotoxicity and the o-chlorophenyl compound kills sugar beets. The m-bromophenyl compound is of interest mainly for control of broadleaf weeds in tomatoes and soybeans, although it may also be used in oats, corn, wheat and

| | | Crab-grass | Cox-comb | Brome | Mil-let | Soy-bean | Cot-ton | Al-fal-fa | Oats | Corn | Flax | Ra-dish | Sugar Beet | Wheat | Grain Sor-ghum | To-mato |
|---|---|---|---|---|---|---|---|---|---|---|---|---|---|---|---|---|
| 2-(m-trifluoro-methylphenyl)-4H-3,1-benzo-azin-4-one; m.p. 129–130.5° | Post | | | | 4 | 4 | 4 | 4 | 1 | 4 | 4 | 4 | 4 | 3 | 3 | 4 |
| | Pre | 0 | 0 | 0 | 0 | 0 | 0 | 0 | 0 | 0 | 0 | 0 | 0 | | | |
| 2-(2-thienyl)-4H-3,1-benzox-azin-4-one; m.p. 139–41° | Post | | | | 4 | 2 | 4 | 4 | 1 | 2 | 4 | 2 | 4 | 4 | 1 | 3 |
| | Pre | 0 | 0 | 0 | 0 | 0 | 0 | 0 | 0 | 0 | 0 | 0 | 0 | | | |
| 2-(o-trifluoro-methylphenyl)-4H-3,1-benzox-azin-4-one; m.p. 100–101° | Post | | | | 3 | 2 | 4 | 2 | 1 | 1 | 4 | 4 | 4 | 1 | 1 | 3 |
| | Pre | 1 | 1 | 4 | 4 | 3 | 2 | 2 | 0 | 0 | 2 | 4 | 1 | | | |
| 2-(p-trifluoro-methylphenyl)-4H-3,1-benzox-azin-4-one; m.p. 104–5° | Post | | | | 4 | 4 | 3 | 4 | 1 | 1 | 4 | 4 | 4 | 1 | 2 | 4 |
| | Pre | 1 | 1 | 4 | 4 | 1 | 1 | 1 | 0 | 0 | 2 | 4 | 1 | | | |
| 2-(4-methyl-1,2,3-thiadiazol-5-yl)-4H-3,1-benzoxazin-4-one; m.p. 168–9° | Post | | | | 2 | 1 | 4 | 4 | 1 | 2 | 4 | 4 | 4 | 1 | 1 | 4 |
| | Pre | 0 | 0 | 0 | 0 | 0 | 0 | 0 | 0 | 0 | 0 | 0 | 0 | | | |
| 2-(m-chloro-phenyl)-4H-3,1-benzoxazin-4-one; m.p. 159–60° | Post | | | | 1 | 1 | 2 | 4 | 1 | 0 | 4 | 4 | 2 | 0 | 0 | 2 |
| | Pre | 0 | 0 | 0 | 0 | 0 | 0 | 0 | 0 | 0 | 0 | 3 | 0 | | | |
| 2-(m-bromo-phenyl)-4H-3,1-benzoxazin-4-one; m.p. 161–2° | Post | | | | 2 | 1 | 2 | 4 | 1 | 1 | 4 | 4 | 4 | 1 | 1 | 2 |
| | Pre | 0 | 0 | 0 | 0 | 0 | 0 | 0 | 0 | 0 | 0 | 0 | 0 | | | |

The tabulated data above illustrate the great variability of properties which occurs even by only a small change in position of the same substituent within this class of compounds. The m-trifluoromethylphenyl compound is useful for controlling both grasses and broadleaf weeds in oats. This ability to kill other grasses in oats is comparatively rare and valuable.

The o-trifluoromethylphenyl compound, however, kills a much smaller group of undesired plants. At somewhat lower application rates it may be used, particularly to combat broadleaf weeds in soybeans, oats, corn, wheat and grain sorghum. This compound is pargrain sorghum. The o-bromo and p-bromo compounds are deficient with respect to desirable herbicidal properties.

I claim:

1. 2-(m-Trifluoromethylphenyl)-4H-3,1-benzoxazin-4-one.

2. 2-(o-Trifluoromethylphenyl)-4H-3,1-benzoxazin-4-one.

3. 2-(p-Trifluoromethylphenyl)-4H-3,1-benzoxazin-4-one.

4. 2-(4-methyl-1,2,3-thiadiazol-5-yl)-4H-3,1-benzoxazin-4-one.

* * * * *